US009528989B2

(12) United States Patent
George et al.

(10) Patent No.: US 9,528,989 B2
(45) Date of Patent: *Dec. 27, 2016

(54) IMAGE-BASED QUANTITATION OF MOLECULAR TRANSLOCATION

(75) Inventors: Thaddeus C. George, Seattle, WA (US); David A. Basiji, Seattle, WA (US); Keith Frost, Seattle, WA (US); Brian E. Hall, Seattle, WA (US); William E. Ortyn, Bainbridge Island, WA (US); Michael J. Seo, Mercer Island, WA (US)

(73) Assignee: Amnis Corporation, Seattle, WA (US)

( * ) Notice: Subject to any disclaimer, the term of this patent is extended or adjusted under 35 U.S.C. 154(b) by 1204 days.

This patent is subject to a terminal disclaimer.

(21) Appl. No.: 13/436,371

(22) Filed: Mar. 30, 2012

(65) Prior Publication Data
US 2012/0244550 A1 Sep. 27, 2012

Related U.S. Application Data

(63) Continuation of application No. 10/593,018, filed as application No. PCT/US2005/008866 on Mar. 16, 2005, now Pat. No. 8,150,136.

(60) Provisional application No. 60/553,484, filed on Mar. 16, 2004, provisional application No. 60/572,877, filed on May 19, 2004.

(51) Int. Cl.
*G06K 9/00* (2006.01)
*G01N 33/569* (2006.01)

(52) U.S. Cl.
CPC .............................. *G01N 33/56966* (2013.01)

(58) Field of Classification Search
USPC 382/128, 129, 133, 134, 209, 278; 128/922, 923
See application file for complete search history.

(56) References Cited

U.S. PATENT DOCUMENTS

| 3,555,280 | A | 1/1971 | Richards, Jr. |
| 3,586,760 | A | 6/1971 | Dillenburger |
| 3,922,069 | A | 11/1975 | Kishikawa et al. |
| 4,313,734 | A | 2/1982 | Leuvering |
| 4,635,293 | A | 1/1987 | Watanabe |
| 4,662,742 | A | 5/1987 | Chupp |
| 4,677,680 | A | 6/1987 | Harima et al. |
| 4,703,017 | A | 10/1987 | Campbell et al. |
| 4,737,932 | A | 4/1988 | Baba |

(Continued)

FOREIGN PATENT DOCUMENTS

| EP | 0154404 A2 | 9/1985 |
| EP | 0280559 A2 | 8/1988 |

(Continued)

OTHER PUBLICATIONS

Amann et al., "Fluorescent-Oligonucleotide Probing of Whole Cells for Determinative, Phylogenetic, and Environmental Studies in Microbiology," Journal of Bacteriology Voi. 172, No. 2: 762-770, Feb. 1990.

(Continued)

*Primary Examiner* — Yosef Kassa
(74) *Attorney, Agent, or Firm* — Lee & Hayes, PLLC

(57) ABSTRACT

The use of an imaging system, cell compartment markers, and molecular markers in methods for correlating the movement of molecules within a cell to a particular compartment are provided, including measuring and correlating molecule movement in adherent and non-adherent cells.

26 Claims, 10 Drawing Sheets

(56) References Cited

U.S. PATENT DOCUMENTS

| | | |
|---|---|---|
| 4,770,992 A | 9/1988 | Van den Engh et al. |
| 4,777,525 A | 10/1988 | Preston, Jr. |
| 4,786,165 A | 11/1988 | Yamamoto et al. |
| 4,845,197 A | 7/1989 | Petersen et al. |
| 4,857,453 A | 8/1989 | Ullman et al. |
| 5,096,807 A | 3/1992 | Leaback |
| 5,107,522 A | 4/1992 | Kitayama et al. |
| 5,122,453 A | 6/1992 | Martin et al. |
| 5,141,609 A | 8/1992 | Sweedler et al. |
| 5,153,916 A | 10/1992 | Inagaki et al. |
| 5,159,397 A | 10/1992 | Kosaka et al. |
| 5,159,398 A | 10/1992 | Maekawa et al. |
| 5,159,642 A | 10/1992 | Kosaka |
| 5,247,339 A | 9/1993 | Ogino |
| 5,247,340 A | 9/1993 | Ogino |
| 5,257,182 A | 10/1993 | Luck et al. |
| 5,272,354 A | 12/1993 | Kosaka |
| 5,351,311 A | 9/1994 | Rogers et al. |
| 5,372,936 A | 12/1994 | Fraatz et al. |
| 5,422,712 A | 6/1995 | Ogino |
| 5,436,144 A | 7/1995 | Stewart et al. |
| 5,444,527 A | 8/1995 | Kosaka |
| 5,459,240 A | 10/1995 | Foxwell et al. |
| 5,471,294 A | 11/1995 | Ogino |
| 5,547,849 A | 8/1996 | Baer et al. |
| 5,548,349 A | 8/1996 | Mizuguchi et al. |
| 5,548,395 A | 8/1996 | Kosaka |
| 5,568,315 A | 10/1996 | Shuman |
| 5,596,401 A | 1/1997 | Kusuzawa |
| 5,621,460 A | 4/1997 | Hatlestad et al. |
| 5,625,048 A | 4/1997 | Tsien et al. |
| 5,633,503 A | 5/1997 | Kosaka |
| 5,644,388 A | 7/1997 | Maekawa et al. |
| 5,674,743 A | 10/1997 | Ulmer |
| 5,686,960 A | 11/1997 | Sussman et al. |
| 5,695,934 A | 12/1997 | Brenner |
| 5,733,721 A | 3/1998 | Hemstreet, III et al. |
| 5,748,162 A | 5/1998 | Hanami |
| 5,754,291 A | 5/1998 | Kain |
| 5,760,899 A | 6/1998 | Eismann |
| 5,764,792 A | 6/1998 | Kennealy |
| RE35,868 E | 8/1998 | Kosaka |
| 5,831,723 A | 11/1998 | Kubota et al. |
| 5,844,670 A | 12/1998 | Morita et al. |
| 5,848,123 A | 12/1998 | Strommer |
| 5,855,753 A | 1/1999 | Trau et al. |
| 5,900,942 A | 5/1999 | Spiering |
| 5,926,283 A | 7/1999 | Hopkins |
| 5,929,986 A | 7/1999 | Slater et al. |
| 5,959,953 A | 9/1999 | Alon |
| 5,985,549 A | 11/1999 | Singer et al. |
| 5,986,061 A | 11/1999 | Pestka |
| 6,007,994 A | 12/1999 | Ward et al. |
| 6,007,996 A | 12/1999 | McNamara et al. |
| 6,014,468 A | 1/2000 | McCarthy et al. |
| 6,066,459 A | 5/2000 | Garini et al. |
| 6,108,082 A | 8/2000 | Pettipiece et al. |
| 6,115,119 A | 9/2000 | Sieracki et al. |
| 6,116,739 A | 9/2000 | Ishihara et al. |
| 6,156,465 A | 12/2000 | Cao et al. |
| 6,159,686 A | 12/2000 | Kardos et al. |
| 6,210,973 B1 | 4/2001 | Pettit |
| 6,211,955 B1 | 4/2001 | Basiji et al. |
| 6,229,913 B1 | 5/2001 | Nayar et al. |
| 6,249,314 B1 | 6/2001 | Yamamoto et al. |
| 6,249,341 B1 | 6/2001 | Basiji et al. |
| 6,256,096 B1 | 7/2001 | Johnson |
| 6,259,807 B1 | 7/2001 | Ravkin |
| 6,330,081 B1 | 12/2001 | Scholten |
| 6,330,361 B1 | 12/2001 | Mitchell et al. |
| 6,381,363 B1 | 4/2002 | Murching et al. |
| 6,473,176 B2 | 10/2002 | Basiji et al. |
| 6,507,391 B2 | 1/2003 | Riley et al. |
| 6,510,319 B2 | 1/2003 | Baum et al. |
| 6,522,781 B1 | 2/2003 | Norikane et al. |
| 6,532,061 B2 | 3/2003 | Ortyn et al. |
| 6,548,259 B2 | 4/2003 | Ward et al. |
| 6,549,664 B1 | 4/2003 | Daiber et al. |
| 6,563,583 B2 | 5/2003 | Ortyn et al. |
| 6,580,504 B1 | 6/2003 | Ortyn et al. |
| 6,583,865 B2 | 6/2003 | Basiji et al. |
| 6,608,680 B2 | 8/2003 | Basiji et al. |
| 6,608,682 B2 | 8/2003 | Ortyn et al. |
| 6,618,140 B2 | 9/2003 | Frost et al. |
| 6,620,591 B1 | 9/2003 | Dunlay et al. |
| 6,658,143 B2 | 12/2003 | Hansen et al. |
| 6,671,044 B2 | 12/2003 | Ortyn et al. |
| 6,707,551 B2 | 3/2004 | Ortyn et al. |
| 6,716,588 B2 | 4/2004 | Sammak et al. |
| 6,727,066 B2 | 4/2004 | Kaser |
| 6,763,149 B2 | 7/2004 | Riley et al. |
| 6,778,263 B2 | 8/2004 | Ortyn et al. |
| 6,873,733 B2 | 3/2005 | Dowski, Jr. |
| 6,875,973 B2 | 4/2005 | Ortyn et al. |
| 6,906,792 B2 | 6/2005 | Ortyn et al. |
| 6,927,922 B2 | 8/2005 | George et al. |
| 6,934,408 B2 | 8/2005 | Frost et al. |
| 6,947,128 B2 | 9/2005 | Basiji et al. |
| 6,947,136 B2 | 9/2005 | Ortyn et al. |
| 6,975,400 B2 | 12/2005 | Ortyn et al. |
| 7,006,710 B2 | 2/2006 | Riley et al. |
| 7,033,819 B2 | 4/2006 | Kim et al. |
| 7,050,620 B2 | 5/2006 | Heckman |
| 7,057,732 B2 | 6/2006 | Jorgenson et al. |
| 7,079,708 B2 | 7/2006 | Riley et al. |
| 7,087,877 B2 | 8/2006 | Ortyn et al. |
| 7,139,415 B2 | 11/2006 | Finkbeiner |
| 7,180,673 B2 | 2/2007 | Dowski, Jr. |
| 7,190,832 B2 | 3/2007 | Frost et al. |
| 7,221,457 B2 | 5/2007 | Jorgenson et al. |
| 7,289,205 B2 | 10/2007 | Yaroslavsky et al. |
| 7,315,357 B2 | 1/2008 | Ortyn et al. |
| 7,450,229 B2 | 11/2008 | Ortyn et al. |
| 7,567,695 B2 | 7/2009 | Frost et al. |
| 7,887,783 B2 * | 2/2011 | Zhao .............. A61K 51/0474 424/1.11 |
| 7,907,769 B2 * | 3/2011 | Sammak .......... G06K 9/00127 382/133 |
| 8,189,900 B2 * | 5/2012 | Sammak .......... G06K 9/00127 382/133 |
| 8,653,034 B2 * | 2/2014 | Thorpe .............. A61K 39/395 514/19.3 |
| 2001/0006416 A1 | 7/2001 | Johnson |
| 2001/0012620 A1 | 8/2001 | Rich |
| 2002/0126275 A1 | 9/2002 | Johnson |
| 2002/0146734 A1 | 10/2002 | Ortyn et al. |
| 2003/0048931 A1 | 3/2003 | Johnson et al. |
| 2003/0049701 A1 | 3/2003 | Muraca |
| 2003/0059093 A1 | 3/2003 | Rosania et al. |
| 2003/0104439 A1 | 6/2003 | Finch |
| 2004/0111220 A1 | 6/2004 | Ochs et al. |
| 2004/0241759 A1 | 12/2004 | Tozer et al. |
| 2005/0014129 A1 | 1/2005 | Cliffel et al. |
| 2006/0246481 A1 | 11/2006 | Finch et al. |
| 2006/0257884 A1 | 11/2006 | Brawley et al. |
| 2008/0240539 A1 | 10/2008 | George et al. |
| 2009/0202130 A1 | 8/2009 | George et al. |

FOREIGN PATENT DOCUMENTS

| | | |
|---|---|---|
| EP | 0281327 A2 | 9/1988 |
| EP | 0372707 A2 | 6/1990 |
| EP | 0950890 A2 | 10/1999 |
| EP | 1316793 A1 | 6/2003 |
| WO | WO8808534 A1 | 11/1988 |
| WO | WO9010715 A1 | 9/1990 |
| WO | WO9520148 A1 | 7/1995 |
| WO | WO9726333 A1 | 7/1997 |
| WO | WO9853093 A1 | 11/1998 |
| WO | WO9853300 A2 | 11/1998 |
| WO | WO9924458 A1 | 5/1999 |
| WO | WO9964592 A2 | 12/1999 |
| WO | WO0006989 A2 | 2/2000 |

(56) References Cited

FOREIGN PATENT DOCUMENTS

| WO | WO0014545 A1 | 3/2000 |
|---|---|---|
| WO | WO0042412 A1 | 7/2000 |
| WO | WO0111341 A2 | 2/2001 |
| WO | WO0146675 A2 | 6/2001 |
| WO | WO0217622 A1 | 2/2002 |
| WO | WO0218537 A2 | 3/2002 |
| WO | WO0235474 A1 | 5/2002 |
| WO | WO02073200 A1 | 9/2002 |
| WO | WO02079391 A2 | 10/2002 |
| WO | WO2005090945 A1 | 9/2005 |
| WO | WO2005098430 A2 | 10/2005 |

OTHER PUBLICATIONS

Arkesteijn et al., "Chromosome Specific DNA Hybridization in Suspension for Flow Cytometric Detection of Chimerism in Bone Marrow Transplantation and Leukemia," Cytometry 19: 353-360, Apr. 1995.

Bains et al., "Flow Cytometric Quantitation of Sequence-Specific mRNA in Hemopoietic Cell Suspension by Primer-Induced in Situ (PRINS) Fluorescent Nucleotide Labeling," Experimental Cell Research 208: 321326, Sep. 1993.

Barren III et al., "Method for Identifying Prostate Cells in Semen Using Flow Cytometry," The Prostate 36: 181-188, 1998.

Bauman et al., "Flow Cytometric Detection of Ribosomal RNA in Suspended Cells by Fluorescent In Situ Hybridization," Cytometry 9: 517-524, 1988.

Baumgartner et al., "Automated Evaluation of Frequencies of Aneuploid Sperm by Laser-Scanning Cytometry (LSC)," Cytometry 44: 156-160, 2001.

Ben-Eliezer et al., "All-optical extended depth of field imaging system," Journal of Optics A: Pure and Applied Optics 5: SI64-S169, 2003.

Biggs et al., "Acceleration of iterative image restoration algorithms" Applied Optics Voi. 36, No. 8: 1766-1775, Mar. 10, 1997.

Boyle et al., "Isolation and Initial Characterization of a Large Repeat Sequence Element Specific to Mouse Chromosome 8," Genomics Voi. 12, No. 3: 517-525,1992.

Callet-Bauchu et al., "Distribution of the cytogenetic abnormality +i(3)( q 10) in persistent polyclonal B-celllymphocytosis: a Fiction study in three cases," British Journal of Haematology 99: 531-536, Dec. 1997.

Ding et al., "Characterization and Quantitation ofNF-KB Nuclear Translocation Induced by Interleukin-1 and Tumor Necrosis Factor-u," The Journal of Biological Chemistry Voi. 273, No. 44: 28897-28905, Oct. 30, 1998.

Disteche et al., "Isolation and characterization of two repetitive DNA fragments located near the centromere of the mouse X chromosome," Cytogenetics and Cell Genetics 39: 262-268, 1985.

Dragowska et al., "Measurement of DNA repeat sequence by flow cytometry," Cytometry Supplement 7: 51, Oct. 1994.

Engvall, Eva. "Enzyme Immunoassay ELISA and EMIT," Methods in Enzymology vol. 70, Part A: 419-439, 1980.

Femandez-Lago et al., "Fluorescent Whole-Cell Hybridization with 16S rRNA-Targeted Oligonucleotide Probes to Identify *Brucella* spp. by Flow Cytometry," Journal of Clinical Microbiology vol. 38, No. 7: 2768-2771, Jul. 2000.

Ferraror et al., "Extended focused image in microscopy by digital holography." Optics Express, vol. 13, No. 15: 6738-6749, 2005.

George et al., "Distinguishing Modes of Cell Death Using the ImageStream Multispectral Imaging Flow Cytometer," Cytometry Part A 59A: 237-245, 2004.

George et al., "Extended depth offield using a logarithmic asp here" Journal of Optics A: Pure and Applied Optics 5: SI57-S163, 2003.

George et al., "Quantitative measurement of nuclear translocation events using similarity analysis of multispectral cellular images obtained in flow," Journal of Immunological Methods 311: 117-129, 2006.

Gordy et al., "Visualization of Antigen Presentation by Actin-Mediated Targeting of Glycolipid-Enriched Membrane Domains to the Immune Synapse ofB cell APCs." Journal of Immunology vol. 172, No. 4: 2030-2038, Feb. 15, 2004.

Hecht, Eugene. "Optics 4th ed." Addison-Wesley Longman, Inc., XP-002465391, ISBN: 0/8053-8566-5,2002.

Hultdin et al., "Telomere analysis by fluorescence in situ hybridization and flow cytometry," Nucleic Acids Research vol. 26, No. 16: 3651-3656, Aug. 15, 1998.

Kubota et al., "Flow Cytometer and Imaging Device Used in Combination." Cytometry 21: 129-132, 1995.

Kubota, Fumio. "Analysis of red cell and platelet morphology using an imaging-combined flow cytometer." Clin. Lab. Haem. 25: 71-76, 2003.

Lauzon et al., "Flow Cytometric Measurement of Telomere Length," Cytometry 42: 159-164, Jun. 2000.

Levron et al., "Sperm chromosome abnormalities in men with severe male factor infertility who are undergoing in vitro fertilization with intracytoplasmic sperm injection," Fertility and Sterility vol. 76, No. 3: 479-484, Sep. 2001.

Lowe et al., "Aneuploid epididymal sperm detected in chromosomally normal and Robertsonian translocation-bearing mice using a new threechromosome FISH method," Chromosoma 105: 204-210, 1996.

Majno et al., "Apoptosis, Oncosis, and Necrosis an Overview of Cell Death," American Journal of Pathology Voi. 146, No. 1: 3-15, Jan. 1, 1995.

Martin et al., "Detection of aneuploidy in human interphase spermatozoa by fluorescence in situ hybridization (FISH)," Cytogenetics and Cell Genetics 64: 23-26, 1993.

Nautiyal et al., "17~-Estradiol induces nuclear translocation of CrkL at the window of embryo implantation," Biochemical and Biophysical Research Communications 318: 103-112, 2004.

Ong et al., "Analysis ofMTF Degradation in the Imaging of Cells in a Flow System," International Journal of Imaging Systems & Technology 5: 243-250, 1994.

Ong et al., "Development of an Image Flow Cytometer," Analytical and Quantitative Cytology and Histology. XIVth International Conference on Medical and Biological Engineering and the VIIth International Conference on Medical Physics, Finland: 375-382, Aug. 1987.

Ong et al., "Optical Design in a Flow System for Imaging Cells," Sciences in Medicine, Voi. 14, No. 2: 74-80, 1991.

Ong, Sim Heng, "Development of a System for Imaging and Classifying Biological Cells in a Flow Cytometer," Doctor of Philosophy Thesis, University of Sydney, School of Electrical Engineering, Aug. 1985.

Ortyn et al., "Extended Depth ofField Imaging for High Speed Cell Analysis" Cytometry Part A 71A: 215-231, 2007.

Pala et al., "Flow cytometric measurement of intracellular cytokines," Journal of Immunological Methods 243: 107-124, 2000.

Pang et al., "Detection of aneuploidy for chromosomes 4,6, 7, 8, 9, 10, 11, 12, 13, 17, 18,21, X and Y by fluorescence in-situ hybridization in spermatozoa from nine patients with oligoasthenoteratozoospermia undergoing intracytoplasmic sperm injection," Human Reproduction Voi. 14, No. 5: 1266-1273, 1999.

Patterson et al., "Detection of HI V-I DNA and Messenger RNA in Individual Cells by PCR-Driven in Situ Hybridization and Flow Cytometry," Science 260: 976-979, May 14, 1993.

Perreault et al., "The Role of Disulfide Bond Reduction during Mammalian Sperm Nuclear Decondensation in Vivo," Developmental Biology 101: 160-167, 1984.

Pinkel et al., "Cytogenetic analysis using quantitative, high sensitivity, fluorescence hybridization," Proceedings of the National Academy of Sciences: Genetics 83: 2934-2938, 1986.

Pollice et al., "Sequential Paraformaldehyde and Methanol Fixation for Simultaneous Flow Cytometric Analysis of DNA, Cell Surface Proteins, and Intracellular Proteins," Cytometry 13: 432-444, 1992.

Ried et al., "Simultaneous visualization of seven different DNA probes by in situ hybridization using combinatorial fluorescence and digital imaging microscopy," Proceedings of the National Academy of Sciences: Genetics 89: 1388-1392, Feb. 1992.

(56) References Cited

OTHER PUBLICATIONS

Robbins et al., "Aneuploidy in sperm of Hodgkin's disease patients receiving NOVP chemotherapy," The American Journal of Human Genetics Voi. 55, No. 3—Supplement: A68 (371), Sep. 1994.

Robbins et al., "Detection of Aneuploid Human Sperm by Fluorescence In Situ Hybridization: Evidence for a Donor Difference in Frequency of Sperm Disomic for Chromosomes I and Y," The American Journal of Human Genetics, 52: 799-807, 1993.

Robbins et ai., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," Reproduction, Fertility and Development 7: 799-809, 1995.

Robbins et al., "Use of Fluorescence in Situ Hybridization (FISH) to Assess Effects of Smoking, Caffeine, and Alcohol on Aneuploidy Load in Sperm of Healthy Men," Environmental and Molecular Mutagenesis 30: 175-183, 1997.

Rufer et al., "Telomere length dynamics in human lymphocyte subpopulations measured by flow cytometry," Nature Biotechnology 16: 743-747, Aug. 1998.

Salzman et al., "Light Scatter: Detection and Usage," Current Protocols in Cytometry Supplement 9: 113.1-1.138.8, 1999.

Satoh et al., "Small Aggregates of Platelets Can Be Detected Sensitively by a Flow Cytometer Equipped With an Imaging Device: Mechanisms of Epinephrine-Induced Aggregation and Antiplatelet Effects of Beraprost." Cytometry 48: 194-201,2002.

Schmid et al., "Evaluation of inter-scorer and inter-laboratory reliability of the mouse epididymal sperm aneuploidy (m-ESA) assay," Mutagenesis Voi. 16, No. 3: 189-195,2001.

Schmid et ai., "Simultaneous Flow Cytometric Analysis of Two Cell Surface Markers, Telomere Length, and DNA Content," Cytometry 49: 96-105,2002.

Schwerin et al., "Quantification of Y Chromosome Bearing Spermatozoa of Cattle Using In Situ Hybridization," Molecular Reproduction and Development 30: 39-43, 1991.

Shi et al., "Aneuploidy in human sperm: a review of the frequency and distribution of aneuploidy, effects of donor age and lifestyle factors," Cytogenetics and Cell Genetics 90: 219-226, 2000.

Timm et al., "Amplification and Detection of a Y-Chromosome DNA Sequence by Fluorescence In Situ Polymerase Chain Reaction and Flow Cytometry Using Cells in Suspension," Cytometry (Communications in Clinical Cytometry) 22: 250-255, 1995.

Timm et al., "Fluorescent in Situ Hybridization En Suspension (FISHES) Using Digoxigenin-qLabeled Probes and Flow Cytometry," Biotechniques vol. 12, No. 3: 362-367, 1992.

Trask et al., "Fluorescence in situ hybridization to interphase cell nuclei in suspension allows flow cytometric analysis of chromosome content and microscopic analysis of nuclear organization," Human Genetics 78:251-259, 1988.

Tucker et al., "Extended depth of field and aberration control for inexpensive digital microscope systems" Optics Express vol. 4, No. 11: 467-474, May 24, 1999.

van Dekken et al., "Flow Cytometric Quantification of Human Chromosome Specific Repetitive DNA Sequences by Single and Bicolor Fluorescent in Situ Hybridization to Lymphocyte Interphase Nuclei," Cytometry 11: 153-164, 1990.

van den Berg et al., "Detection of Y Chromosome by In situ Hybridization in Combination with Membrane Antigens by Two-Color Immunofluorescence," Laboratory Investigation vol. 64, No. 5: 623-628, 1991.

Wang et al., "A Novel Apoptosis Research Method With Imaging-Combined Flow Cytometer and HITC OR IR-125 Staining," Cytometry (Clinical Cytometry) 50: 267-274,2002.

Weber-Matthieson et al., "Rapid immunophenotypic characterization of chromosomally aberrant cells by the new Fiction method," Cytogenetics Cell Genetics 63: 123-125, 1993.

Weber-Matthieson et al., "Simultaneous Fluorescence Immunophenotyping and Interphase Cytogenetics: A Contribution to the Characterization of Tumor Cells," Journal of Histoch em is try and Cytochemistry vol. 40, No. 2: 171-175, 1992.

Wietzorrek et ai., "A New Muitiparameter Flow Cytometer: Optical and Electrical Cell Analysis in Combination With Video Microscopy in Flow," Cytometry 35: 291-301, 1999.

Wyrobek et ai., "Detection of Sex Chromosomal Aneuploidies X-X, Y-Y, and X-Y, in Human Sperm Using Two-Chromosome Fluorescence in Situ Hybridization," American Journal of Medica I Genetics 53: 1-7, 1994.

Wyrobek et ai., "Fluorescence in Situ Hybridization to Y Chromosomes in Decondensed Human Sperm Nuclei," Molecular Reproduction and Development 27: 200-208, 1990.

Wyrobek et ai., "Smokers produce more aneuploid sperm than non-smokers," The American Society of Human Genetics, 45th Annual Meeting, A131: 737, Oct. 24-28, 1995.

\* cited by examiner

IMAGE-BASED QUANTITATION OF MOLECULAR TRANSLOCATION

RELATED APPLICATIONS

This Application is a continuation of U.S. patent application Ser. No. 10/593,018, filed on Oct. 22, 2008 and now issued as U.S. Pat. No. 8,150,136, which is a 371 of PCT/US05/08866 filed on Mar. 16, 2005, which claims benefit of U.S. Provisional Application No. 60/553,484 filed on Mar. 16, 2004, and also claims benefit of U.S. Provisional Application No. 60/572,877, filed on May 19, 2004, all of which are hereby incorporated by reference herein in their entirety.

BACKGROUND OF THE INVENTION

Field of the Invention

The present disclosure relates generally to methods for detecting specific molecules in cells, and more specifically, to the use of imagery in methods for quantitating the movement of molecules within a cell, including adherent and non-adherent cells.

Description of the Related Art

Signal transduction pathways regulate most cellular biological processes and have a critical influence on cellular responses to external stimuli. Typically, cell surface receptors that bind to a specific extracellular mediator trigger a cascade of intracellular signaling events that alter cellular metabolism or gene expression, and such changes contribute to the cellular response. The intracellular signaling cascade often involves the translocation of transcription factors or second messengers from the cytoplasm to the nucleus.

Historically, nuclear translocation events have been studied microscopically by observing the sub-cellular localization of fluorescent probe-labeled signaling molecules. Until recently, microscopic applications have been limited due to the subjective nature and the lack of means to quantitate imagery. Currently, several quantitative plate based microscopy platforms are available that attempt to quantitate translocation (ArrayScan, Cellomics, Inc. (Pittsburgh, Pa.); Laser Scanning Cytometer, Compucyte Corporation (Cambridge, Mass.); IN Cell Analyzer, Amersham International plc. (Little Chalfont, England)). However, these microscopy platforms typically rely on the use of adherent cell lines, and their biological responses may differ from suspension-type cells (which include most blood cells).

Traditionally, the measurement of the translocation of fluorescently bound molecules into the nucleus has been determined by a method referred to as the Nuc-Cyt difference (Ding et al., *J. Biol. Chem.* 273:28897, 1998). This measurement involves the following steps: (1) determining the boundaries of the nucleus which has been stained with a nuclear stain; (2) eroding the mask or area contained within the boundaries to insure the entire area is within the nucleus; (3) summing up the total fluorescence intensity associated from the labeled molecules of interest (Total Nuclear Fluorescence); (4) dilating the nuclear boundary to determine an annular ring solely contained in the cytoplasm and integrate the fluorescence associated with the labeled molecule of interest (Annular Cytoplasm Fluorescence); and (5) calculating the difference between the Total Nuclear and Annular Cytoplasm Fluorescence to yield the Nuc-Cyt difference. However, this method is unlikely to produce the best measurement because it relies on an accurate nuclear mask, subjective erosion and dilation routines that determine the nuclear' and cytoplasmic boundaries, an additional subjective dilation of the cytoplasm mask to create an annular volume, and both the cytoplasm and the nucleus have areas that are not represented in the calculation.

Thus, the need exists for techniques that can allow quantitation of molecular Transport, such as nuclear translocation, in cells in flow to afford the opportunity to study suspension-based cell lines as well as primary cells. For example, such techniques would allow detailed analysis of nuclear translocation responses in subset of cells, such as blood cells. The present invention meets such needs, and further provides other related advantage.

DETAILED DESCRIPTION

The instant disclosure relates to the use of multi-mode imagery of cells, including in non-adherent and adherent cell types, to monitor or identify molecular processes and movement in and between all cellular compartments. An advantage of the methods provided in the instant disclosure is that the shortcomings of the Nuc-Cyt difference calculation discussed above are generally obviated. Specifically, the methods of the instant disclosure use a measurement based upon statistical correlation, referred to herein as Compartmental Correlation Feature (CCF), which is a more robust method than the Nuc-Cyt calculation because (i) a single Nuclear Mask is used, (ii) spatial information is taken into account, (iii) subjective dilation, erosion, and annular dilation routines are not required, and (iv) the entire cellular nucleus is taken into account. Discussed in more detail below are single-step methods of using morphometric and photometric features from comprehensive multispectral imagery, in combination with CCF, to permit the analysis or observation of, for example, molecular movement or transport into a cell, out of a cell, within a cell, or between subcellular compartments. Thus, it should be understood that reference herein to "movement of a molecule in a cell" encompasses movement or transport of a molecule or molecules into a cell, out of a cell, within a cell, or between subcellular compartments, and combinations thereof. An exemplary image system for use with the methods in the instant disclosure is an ImageStream® 100 multispectral imaging flow cytometer platform, which produces high-resolution brightfield, darkfield, and fluorescence images with the simplified sample handling and quantitative power of flow cytometry. In addition, the IDEAS™ analysis software can quantify over 200 photometric and morphometric parameters for each cell that passes through the imaging system, including parameters that can quantify the cellular and sub-cellular location of molecules, probes, and other indigenous or exogenous compounds within a cell.

In the present description, any concentration range, percentage range, or integer range is to be understood to include the value of any integer within the recited range and, when appropriate, fractions thereof (such as one tenth and one hundredth of an integer, etc.), unless otherwise indicated. As used herein, the term "about" means ±15%. As used herein, the use of an indefinite article, such as "a" or "an", should be understood to refer to the singular and the plural of a noun or noun phrase (i.e., meaning "one or more" of the enumerated elements or components). The use of the alternative (e.g., "or") should be understood to mean either one, both or any combination thereof of the alternatives.

Figure 1:
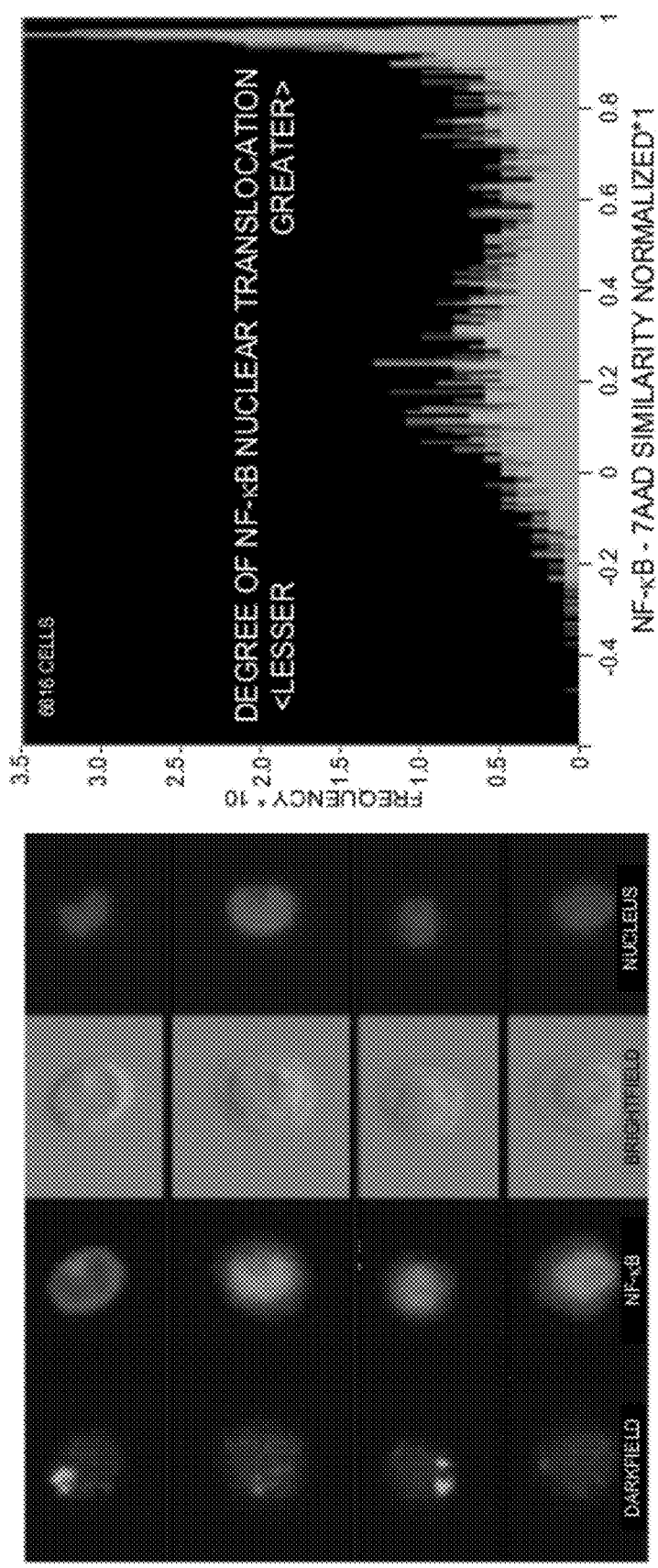
FIG. 1 shows nuclear translocation of NF-κB in immune cells. The left panel shows a monocytic cell line imaged simultaneously in darkfield, green fluorescence (fluorescein isothiocyanate (FITC) labeled anti-NF-κB), brightfield, and red fluorescence (nuclear stain 7-aminoactinomycin D). Each image row represents a different, single cell. The first cell is untreated and cells 2-4 have been treated with lipopolysaccharide (LPS). The right panel is a statistical analysis of the imagery that quantitatively characterizes the degree of NF-κB translocation to the nucleus.

By way of background, methodologies for simultaneous high speed multispectral imaging in brightfield, darkfield, and four channels of fluorescence of cells in flow were recently developed (see, e.g., U.S. Pat. Nos. 6,211,955 and 6,249,341). FIG. 1 illustrates an exemplary imaging system (e.g., the ImageStream platform). Cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with ail object.

Prior to projection on the CCD, the light is passed through a spectral decomposition optical system that directs different spectral bands to different lateral positions across the detector (see. e.g., U.S. Pat. No. 6,249,341). With this technique, an image is optically decomposed into a set of 6 sub-images, each corresponding to a different color component and spatially isolated from the remaining sub-images. This process allows for identification and quantitation of signals within the cell by physically separating on the detector signals that may originate from overlapping regions of the cell. Spectral decomposition also allows multimode imaging: the simultaneous detection of brightfield, darkfield, and multiple colors of fluorescence. This is exemplified in FIG. 1, which depicts a red brightfield illumination source and the associated transmitted light images in the red detector channel adjacent to fluorescent and scattered light images in the other spectra) channels. The process of spectral decomposition occurs during the image formation process rather than via digital image processing of a conventional composite image.

The CCD may be operated using a technique called time-delay-integration (TDI), a specialized detector readout mode that preserves sensitivity and image quality even with fast relative movement between the detector and the objects being imaged. As with any CCD, image photons are converted to photo charges in an array of pixels. However, in TDI operation the photocharges are continuously shifted from pixel to pixel down the detector, parallel to the axis of flow. If the photocharge shift rate is synchronized with the velocity of the flowing cell's image, the effect is similar to physically panning a camera: image streaking is avoided despite signal integration times that are orders of magnitude longer than in conventional flow cytometry. For example, an instrument may operate at a continuous data rate of approximately 30 megapixels per second and integrate signals from each object for 10 milliseconds, allowing the detection of even faint fluorescent probes within cell images that are acquired at high-speed. Careful attention to pump and fluidic system design to achieve highly laminar, non-pulsatile flow eliminates any cell rotation or lateral translation on the time scale of the imaging process (see, e.g., U.S. Pat. No. 6,532,061).

A real-time algorithm analyzes every pixel read from the CCD to detect the presence of object images and calculate a number of basic morphometric and photometric features, which can be used as criteria for data storage. Data files encompassing 10,000-20,000 cells are typically about 100 MB in size and, therefore, can be stored and analyzed using standard personal computers. The TDI readout process operates continuously without any "dead time," which means every cell can be imaged and the coincidental imaging of two or more cells at a time presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc. As used herein, morphological parameters may be basic (e.g., nuclear shape) or may be complex (e.g., identifying cytoplasm size as the difference between cell size and nuclear size). For example, morphological parameters may include nuclear area, perimeter, texture or spatial frequency content, centroid position, shape (i.e., round, elliptical, barbell-shaped, etc.), volume, and ratios of any of these parameters. Morphological parameters may also include cytoplasm size, texture or spatial frequency content, volume and the like, of cells. As used herein, photometric measurements with the aforementioned imaging system can enable the determination of nuclear optical density, cytoplasm optical density, background optical density, and the ratios of any of these values. An object being imaged can be stimulated into fluorescence or phosphorescence to emit light, or may be luminescent wherein light is produced without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object. In using an imaging system as described herein, it should be made clear that a separate light source is not required to produce an image of the object (cell), if the object is luminescent (i.e., if the object produces light). However, many of the applications of an imaging system as described herein will require that one or more light sources be used to provide light that is incident on the object being imaged. A person having ordinary skill in the art will know that the location of the light sources substantially affects the interaction of the incident light with the object and the kind of information that can be obtained from the images on a TDI detector.

In addition to imaging an object with the light that is incident on it, a light source can also be used to stimulate emission of light from the object. For example, a cell having been contacted with probe conjugated to a fluorochrome (e.g., FITC, PE, APC, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by prism. The disposition of these fluorescent spots on the TDI detector surface will depend upon their emission spectra and their location in the object.

Each light source may produce light that can either be coherent, non-coherent, broadband or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, preferably a pulsed laser. If a pulsed type illumination source is employed, the extended integration period associated with TDI detection can allow the integration of signal from multiple pulses. Furthermore, it is not necessary for the light to be pulsed in synchronization with the TDI detector.

The present disclosure provides methods of using both photometric and morphometric features derived from multimode imagery of objects in flow. Such methods can be employed to analyze molecular movement within or between cells, in heterogeneous populations of cells when entrained in a fluid flowing through an imaging system. As used herein, cells may be eukaryotic or prokaryotic or viral, human, non-human animal, plant, unicellular, a primary cell culture or culture-adapted cell line, immortalized or immortalizable, differentiated or differentiatable, and the like. In addition, cells may be genetically engineered (transduced, transformed or transfected) with one or more chromosomally integrated or episomal recombinant nucleic acid sequences. The cells may have been exposed to one or more chemicals or compounds to induce or repress signaling pathways (e.g., signal transduction pathway) or other cellular function. However, it should be understood that these cells and exemplary methods might be used for imaging and distinguishing other moving objects that have identifiable photometric and morphometric features, such as systems biology structures (cytomic objects), liposomes, polymeric microspheres or capsules, nanostructures, nanomolecules, and the like.

In the embodiments of the present invention, it is to be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion, which movement may be in different directions and/or at different rates.

In any of the aforementioned methods, multiple images may be collected simultaneously. Furthermore, in any of the aforementioned methods, there is relative motion between the cell and the detector. In addition, in any of the aforementioned methods, the detector is a time delay integration charge-coupled detector.

Compartmental Correlation Feature

As set forth above, the methods of the instant disclosure have been designed to overcome the shortcomings of the Nuc-Cyt difference calculation when monitoring, for example, nuclear translocation. That is, the Nuc-Cyt calculation requires, among other routines, accurate determination of a nuclear mask, subjective erosion and dilation routines that determine the nuclear and cytoplasmic boundaries, and subjective dilation of the cytoplasm mask to create an annular volume. The instant disclosure provides the use of an imaging system to track or correlate the movement of a molecule in a cell using a calculation referred to as Compartmental Correlation Feature (CCF). For example, using the multispectral imaging capabilities of an imaging system (e.g., ImageStream®), at least two different spectral images are collected corresponding to the emission wavelengths of a fluorescent dye specific for a cellular compartment (e.g., nucleus, mitochondria, cytoplasm, membrane) and a fluorescent dye specific for a translocated molecule. A cellular compartment mask may be generated based on the cellular compartment stain image, then a correlation measurement is made between the cellular compartment mask and the dye area of the translocated molecule. Consequently, molecules that are translocated to the targeted cellular compartment should have a high correlation (i.e., the images should show significant overlap), whereas cell lacking cellular compartment translocation should have a low correlation (i.e., images that show less of an overlap). The correlation value for each cell can be plotted as a histogram, which will display the degree of cellular compartment translocation of a molecule for a cell population. Furthermore, as noted above, the CCF can be used to determine or analyze molecular movement within any cellular compartment, such as translocation to or from the nucleus, movement to or from the cytoplasm, or movement to or from a cellular membrane, etc., and combinations thereof.

FIG. 1 illustrates the case of a nuclear translocation assay where a fluorescent nucleic acid binding dye, 7-aminoactinomycin D (7-AAD, shown as red fluorescence), is used to stain the nucleus, while a different fluorescent marker (green; e.g., a FITC conjugated antibody) is used to label a translocating molecule of interest (e.g., NF-κB). Using the multispectral imaging capabilities of the ImageStream®, at least two different spectral images are collected, corresponding to the emission wavelengths of the nuclear fluorescent dye and the fluorescent dye on the molecule NF-κB (to track translocation). A nuclear mask is generated from the nuclear stain image and then a correlation measurement is made between the nuclear mask area of both fluorescence channels. Cells that exhibited nuclear translocation of NF-κB had a high correlation (see, e.g., FIG. 1, image rows 2-4), while cells with low nuclear translocation had a low correlation (see, e.g., FIG. 1, image row 1). The correlation value for each cell was plotted as a histogram, which displays the degree of NF-κB nuclear translocation for the cell population (see, e.g., FIG. 1, graph on right).

Compartmental Correlation Feature Calculation

Compartmental Correlation is a measurement based upon a statistical definition of correlation. The correlation of X and Y is the measurement defined by:

$$\rho(X,Y) = Cov(X,Y)/(\sigma X \sigma Y).$$

where X and Y are the fluorescent nuclear and trans locating molecule images.

Cov(X,Y) is the covariance of X and Y and is defined by:

$$Cov(X,Y) = \text{Expected Value of } [X-\mu X)(Y-\mu Y)]$$

Also, μX,σX and μY, σY are the mean and standard deviations of X and Y, respectively. The measurement ρ(X, Y) is also known as the correlation coefficient. Correlation is most effective in measuring relationships between X and Y that are linear.

Similarity is correlation, which is applied to imagery where X and Y are the pixel representations of imagery. First, begin by defining the mask, M. M is the set of coordinates (i,j). Let N=the number of elements in the set M. Then $$\mu X = \Sigma X(i,j)/N \text{ and } \sigma X = \text{sqrt}\{\Sigma(X(i,j)-\mu X)(X(i,j)-\mu X))/(N-1)\},$$

$$\mu Y = \Sigma Y(i,j)/N \text{ and } \sigma X = \text{sqrt}\{\Sigma(Y(i,j)-\mu Y)(Y(i,j)-\mu Y))/(N-1)\},$$

$$Cov(X,Y) = \Sigma(X(i,j)-\mu X)(Y(i,j)-\mu Y))/(N-1).$$

When Compartmental Correlation is applied to images that exhibit molecular movement or translocation, this value tends to shift closer to a value of 1.0. When the images reveal lack of molecular movement or translocation (un-translocation), this value tends to shift closer to a value of −1.0. The Compartmental Correlation measurement and the imagery indicate that the different degree of translocation of NF-κB into the nucleus is a linear relationship. Therefore, Compartmental Correlation is optimal for measuring such a relationship.

Mask Determination

In order for the correlation between pixel intensities to provide unambiguous evidence for or against the co-location of probes (e.g., labeled molecules) in cells, an appropriate subset of pixels should be selected over which the correlation is to be computed. If, for example, background pixels not belonging to the cell of interest are included in the set, a strong positive correlation may be found, even when the probes tend to separate within the cell because both probes are present in larger quantities within the cell than outside the cell. In general, a variety of chemical, morphological, and intensity-based methods may need to be applied in a given experiment to select the pixels of interest.

In the example of nuclear translocation: the task of selecting the pixels of interest is simplified by the presence of the nuclear probe. In this assay, the pixels of interest are those directly illuminated by the nucleus and cytoplasm. The presence of the nuclear probe means that all that is usually needed to get a sufficiently accurate set of pixels is a mask based on a blurred image of the nuclear probe, perhaps extended to include regions (near the nucleus) where the nuclear probe intensity is varying sufficiently rapidly. In the case of membrane probes, certain parameters should be chosen, such as a narrow band of pixels right on the edge of the cell, while excluding from consideration those either on the interior or exterior. Morphological criteria will play a role in constructing an appropriate set of pixels in the case of membranes and the morphology required is of two types. The first is a local constraint, requiring the band of pixels of increased intensity to be sufficiently narrow in order to qualify as a piece of the membrane. The second is a more global criterion, requiring that the band of pixels be sufficiently close to the global boundary defining the interior of the cell.

Uses

A multispectral imaging system and CCF can be used in a variety of applications, including diagnostics, drug discovery, and the like. For example, an imaging system may be used to identify compounds that affect or alter the activation of transcription factor NF-κB in cells of the immune system. Immune cells may be contacted with particular chemicals, cytokines, or environmental agents to examine whether translocation of the NF-κB molecule from the cytoplasm to the nucleus occurs as part of an immune response. The quantitative measurement of the amount of NF-κB in the nucleus versus the cytoplasm may, therefore, be extremely useful in the development of drugs that target immune function. Conventional high content screening systems are hindered in the analysis of NF-κB distribution due to the difficulty of imaging non-adherent immune cells on slides or plates and accurately measuring the quantity of NF-κB in the thin band of cytoplasm that characterize immune cells. The ImageStream platform, for example, eliminates these constraints with its ability to image non-adherent cells directly in suspension, its high resolution, and the statistical power (e.g., use of CCF) associated with its ability to analyze tens of thousands of cells.

Figure 7:
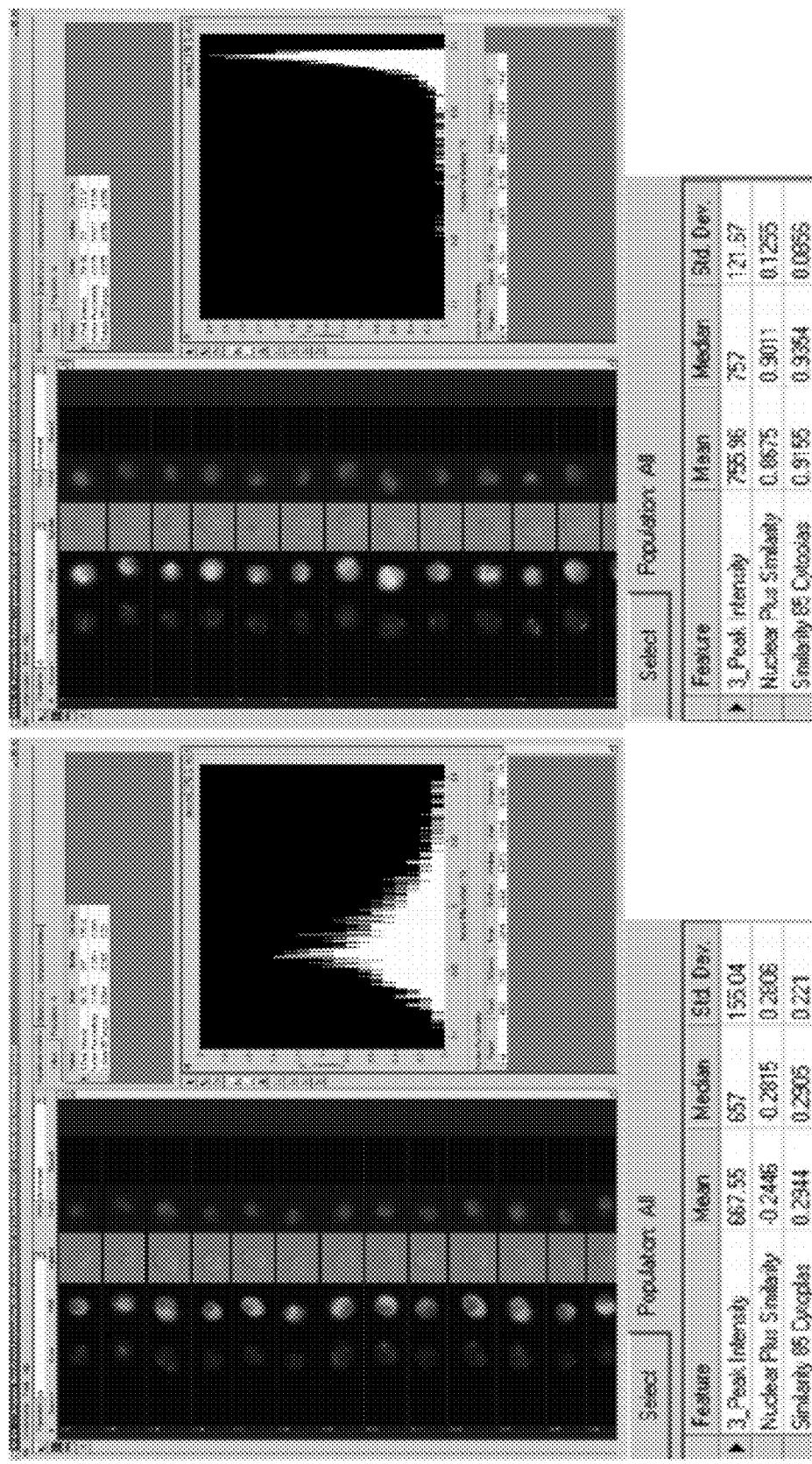
FIG. 7 shows images of nuclear translocation of NF-κB in adherent A-549 cells untreated (from left, first panel, images; second panel, quantitation of first panel images) and treated with IL-1β/TNF-α (third panel, images; fourth panel, quantitation of third panel images). Images are from darkfield, NF-κB labeled, brightfield, and 7-AAD nuclear label.
Figure 8:
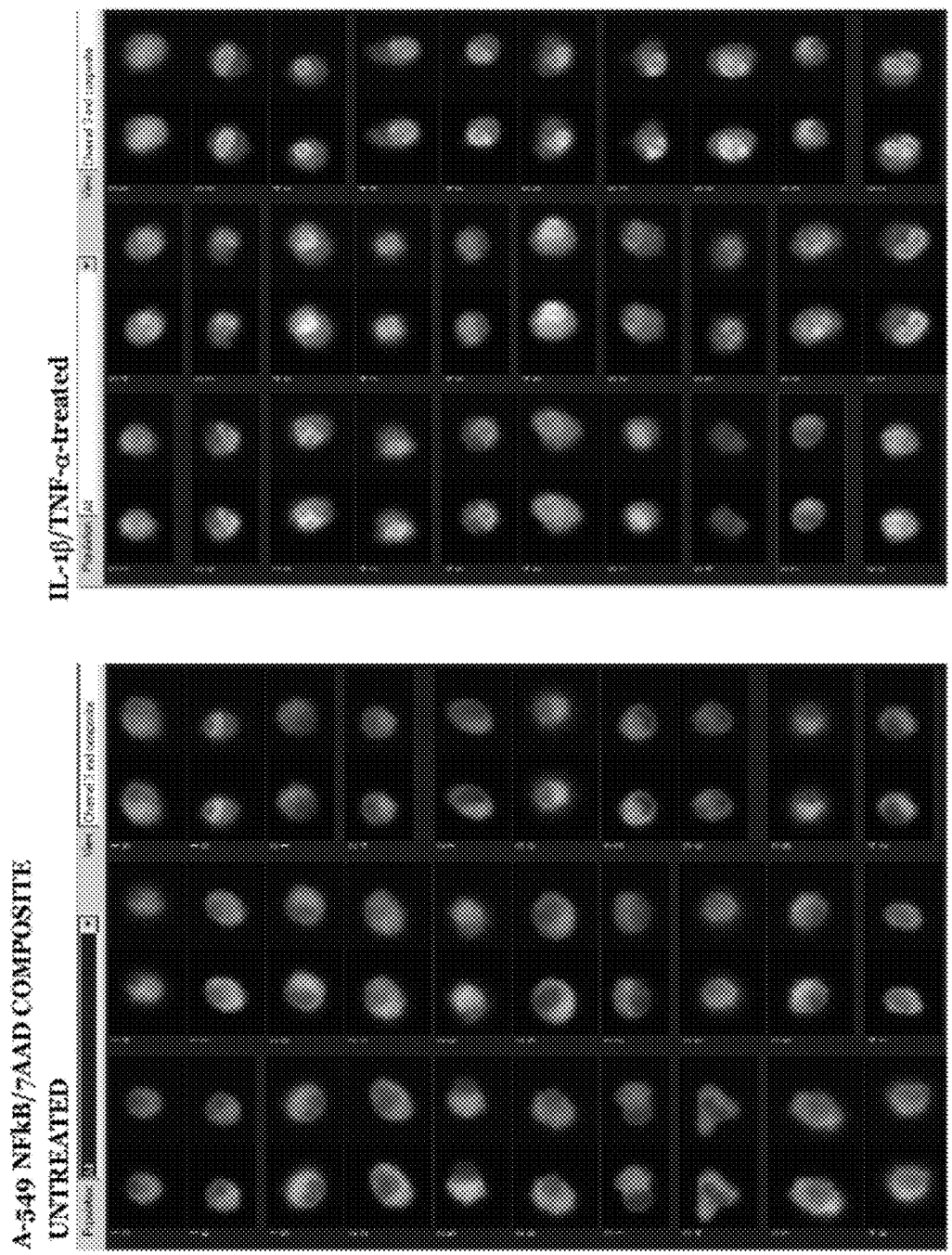
FIG. 8 shows images of nuclear translocation of NF-κB in A-549 cells untreated (left panel) and treated with IL-1β/TNF-α (right panel). Images include brightfield and a composite of cells stained with anti-NF-κB and with 7-AAD.
Figure 9:
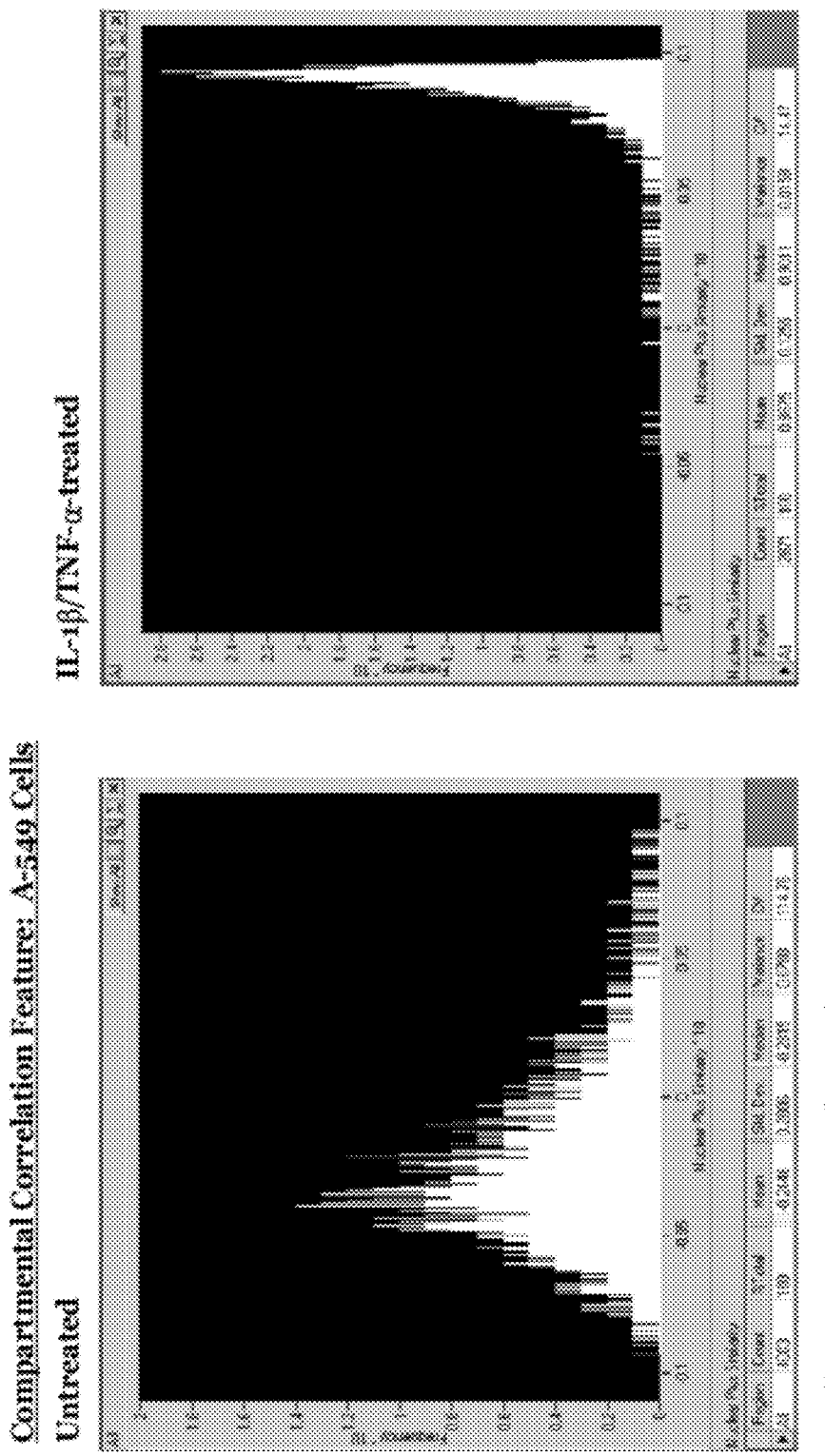
FIG. 9 shows quantitation of compartmental correlation feature in untreated and IL-1β/TNF-α-treated A-549 cells.

By way of background, it is well established that Tumor Necrosis Factor-α (TNF-α) and Interleukin 1-β (IL-1β) induce translocation of NF-κB from the cytoplasm to the nucleus in many cell types. In FIG. 7, an adherent human lung carcinoma cell line A-549 was either not treated or treated for 1 hr with IL-1β and TNF-α. The cells were trypsinized and washed off the plate to adapt the cells to flow, and probed for NF-κB (stained with anti-NF-κB mAb-AF488 donkey anti-mouse IgG). The nucleus was also stained with 7-AAD. Using ImageStream and the CCF, a quantifiable difference in the nuclear localization NF-κB was observed when comparing untreated and IL-1β/TNF-α treated cells (see FIGS. 7 and 9). Thus, the methods of the present disclosure may be used with adherent cells and cell lines.

Figure 2:
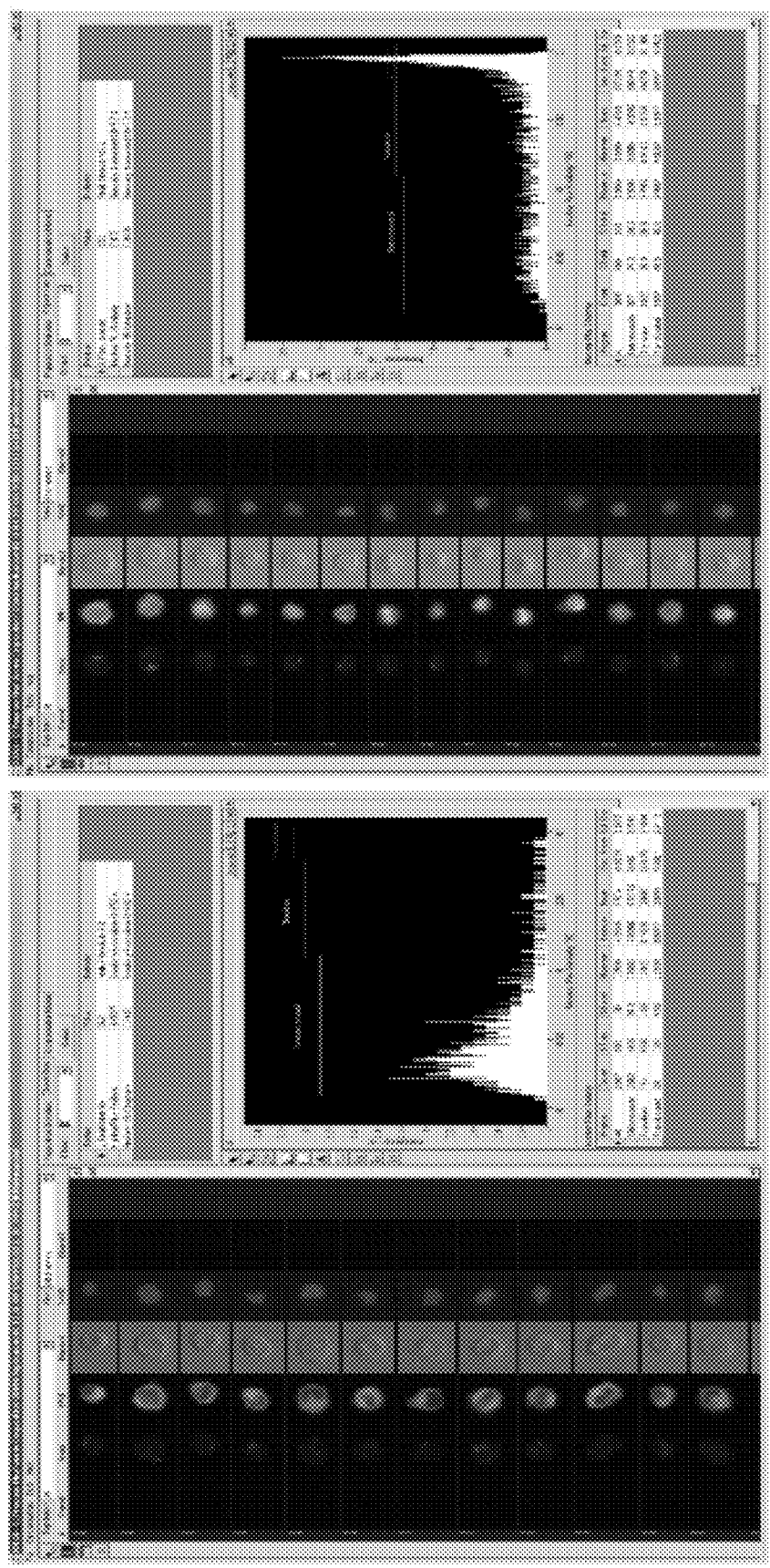
FIG. 2 shows nuclear translocation of NF-κB in THP-1 cells (monocyte cell line) untreated (from left, first panel, images; second panel, quantitation of first panel images) and treated with LPS (third panel, images; fourth panel, quantitation of third panel images). Images are from darkfield, NF-κB labeled, brightfield, and 7-AAD nuclear label.
Figure 3:
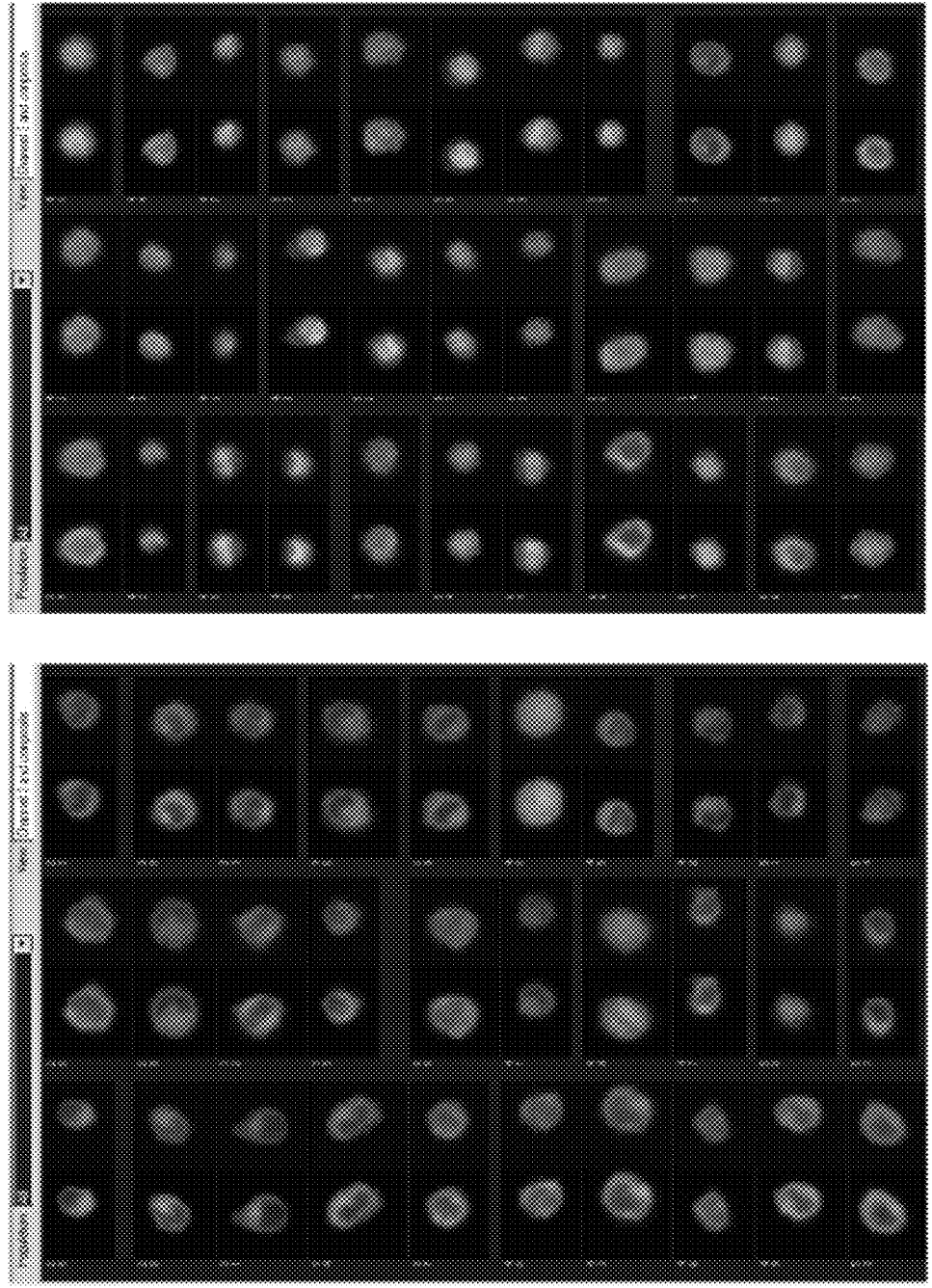
FIG. 3 shows images of nuclear translocation of NF-κB in THP-1 cells untreated (left panel) and treated with LPS (right panel). Images include brightfield and a composite of cells stained with anti-NF-κB and with 7-AAD.
Figure 4:
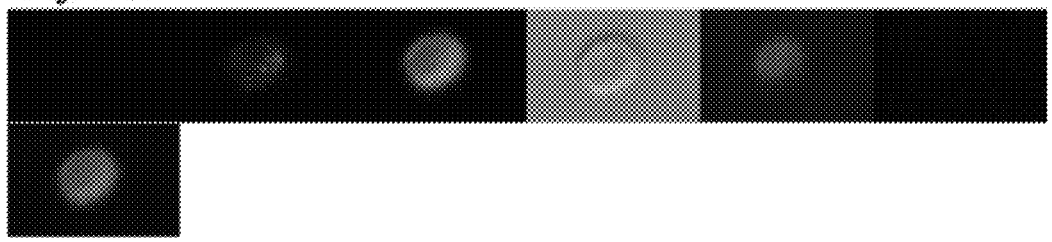
FIG. 4 shows 7-AAD mask and NF-κB mask used in a compartmental correlation feature calculation.
Figure 4:
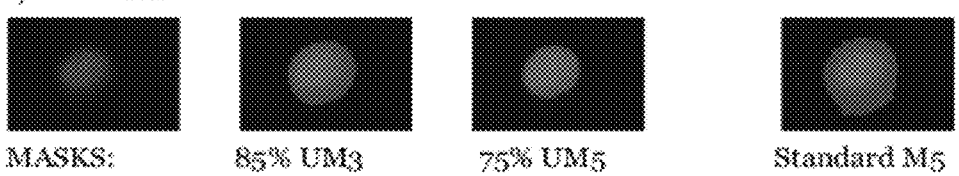
Figure 4:
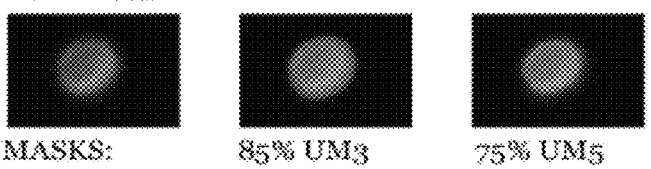
Figure 5:
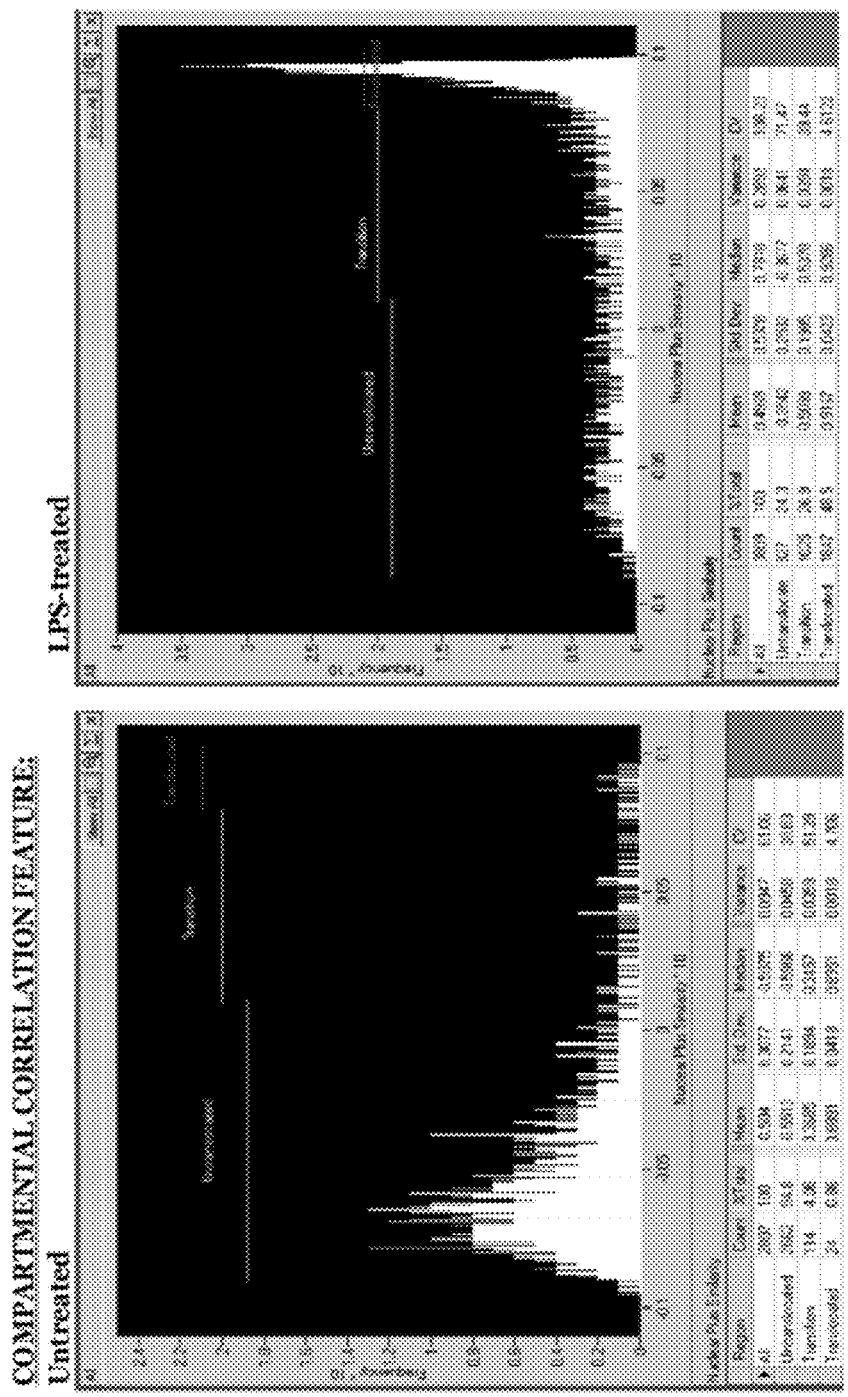
FIG. 5 shows quantitation of compartmental correlation feature in untreated and LPS-treated THP-1 cells.
Figure 6A:
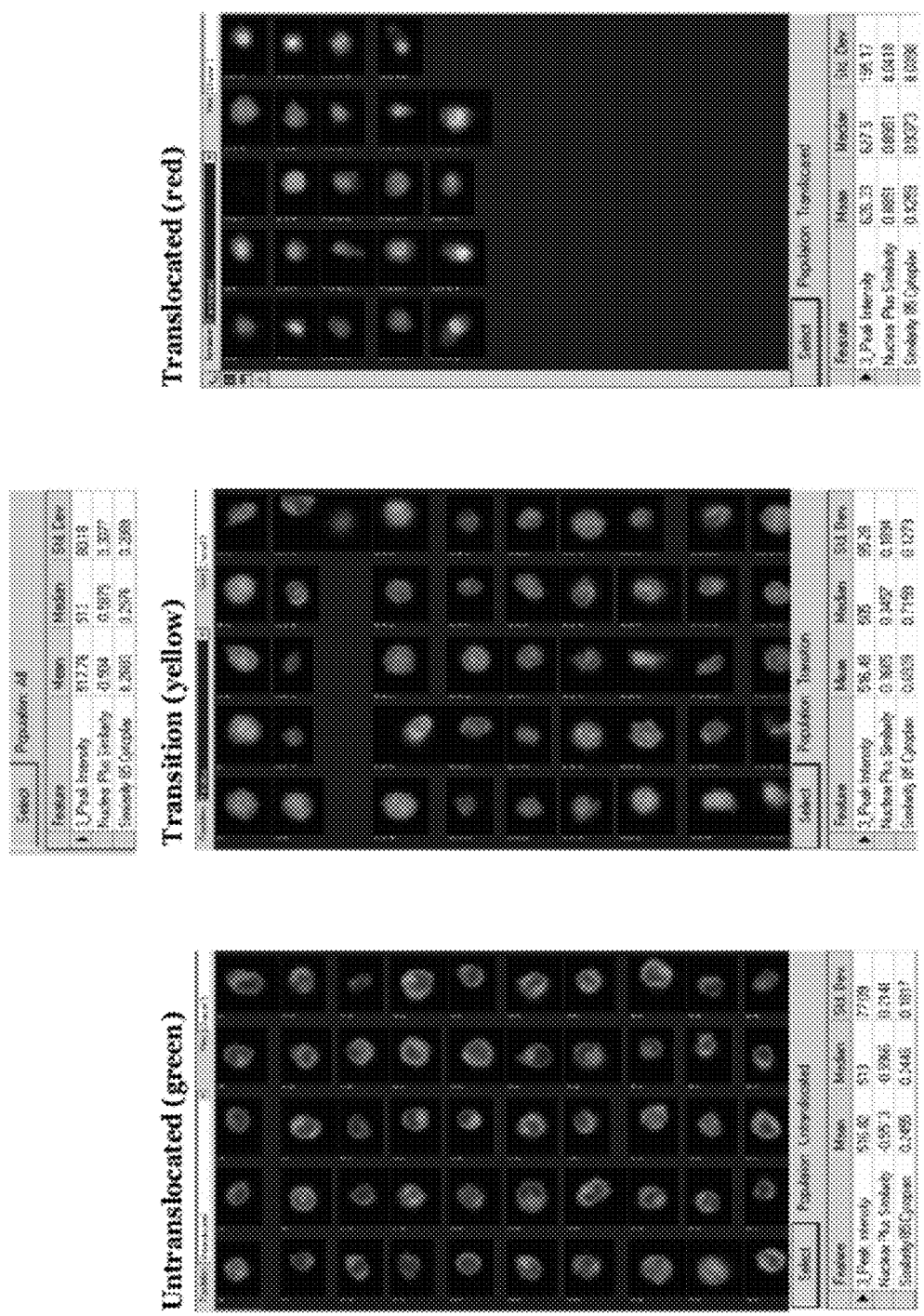
FIGS. 6A and 6B show imagery of THP-1 cells (A) untreated and (B) LPS-treated, and the three populations (untranslocated—green, transitional—yellow, and translocated—red) identified in the quantitation of FIG. 5.
Figure 6B:
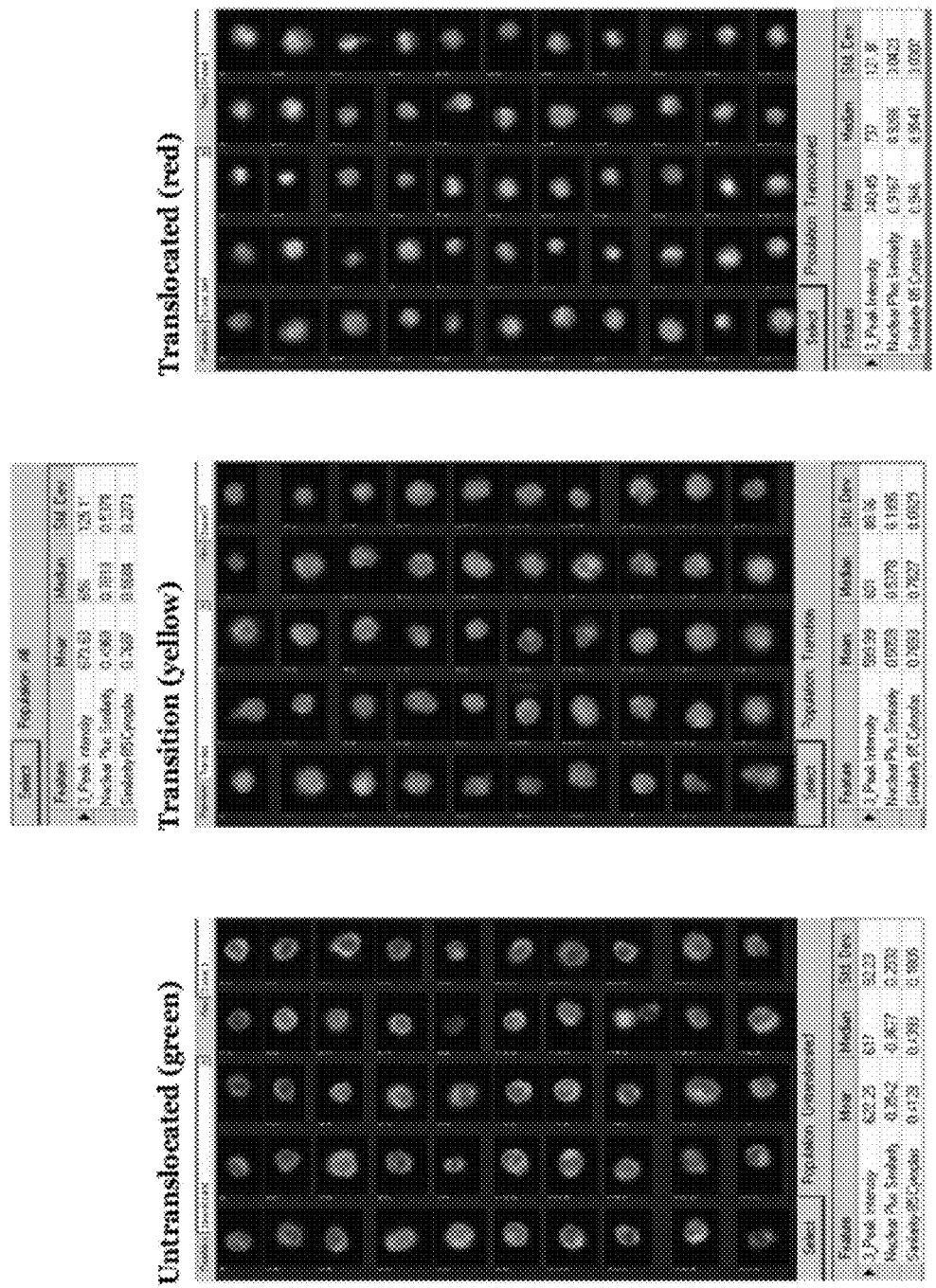

By way of background and without wishing to be bound by theory, NF-κB resides predominantly in the cytoplasm in resting cells. Activating treatments (e.g., IL-1β/TNF-α or LPS) induce NF-κB translocation into the nucleus in responsive cell types. Thus, the ratio of nuclear to cytoplasmic NF-κB increases with LPS treatment. Similar to the A-549 cells, NF-κB is translocated from the cytoplasm to the nucleus when the non-adherent human monocyte cell Line, THP-I, is exposed to lipopolysaccharide (LPS). Using the identical probing protocol and CCF, again a quantifiable difference in the nuclear localization NF-κB is demonstrated when comparing untreated and LPS-treated cells (see FIGS. 2 and 5). A nuclear and NF-κB pixel signal correlation analysis CCF was used to quantitate the difference between untranslocated NF-κB and NF-κB translocated to the cell nucleus. The CCF distinguished location-specific (nuclear and cytoplasmic) quantitation of NF-κB to distinguish LPS-treated from untreated THP-I cells. Thus, the methods of the present disclosure may also be used with non-adherent cells and cell lines.

Classifier Approach: Compartmental Correlation Feature Scoring

The CCF is an algorithmic feature that correlates the variation of pixels (from the mean) across two channels, in this case the 7-AAD (nuclear) and NF-κB channels, within a generous 75% 7-AAD mask. This feature reduces cell-to-cell variation judgment calls associated with integrated nuclear to cytoplasmic NF-κB intensity ratios. This feature also avoids cell-to-cell variation in the inclusion/expulsion of background-like pixels associated with user defined NK-κB masks (see FIGS. 5 and 9).

All of the U.S. patents, U.S. patent application publications, U.S. patent applications, foreign patents, foreign patent Application and non-patent publications referred to in this specification and/or listed in the Application Data Sheet, are incorporated herein by reference, in their entirety. The invention having been described, the following examples are intended to illustrate, and not limit, the invention.

EXAMPLES

Example 1

Induction of Translocation in Adherent Cells

Human lung carcinoma cell line A-549, obtained from ATCC (Rockville, Md.), was maintained in RPMI 1640 (Gibco, Grand Island, N.Y.) containing 5% fetal bovine serum, 1 mM sodium pyruvate (Mediatech, Herndon, Va.), 100 μM nonessential amino acids, 100 U/ml penicillin, 100 μg/ml streptomycin, and 2 mM L-glutamine (BioWhittaker, Walkersville, Md.) in 5% $CO_2$ atmosphere at 37° C. The density of exponentially growing cells was less than $3 \times 10^5$ cells per ml at the time of all treatments. To induce NF-κB translocation into the nucleus from the cytoplasm, cells were treated for 1 hr with IL-10 and TNF-α.

The following is the experimental procedure for TNF-α/IL-1β induced Nuclear Translocation of NF-κB in A-549 cells.
Samples:
1) Unstained and single fluorescent color control samples—
 start with $3.0 \times 10^6$ total cells each. In this experiment, controls are: unstained
 NFκB Alexa Fluor488
 7-AAD
At the end, resuspend in 100 μl 0.1% triton X-100/PBS.
Unstained and NF-κB can be mixed and run as one file, then a separate raw image file (.rif) of unlabeled cells can be created in IDEAS. The 7-AAD control must be run separately, because 7-AAD comes off of labeled cells and stains unlabeled cells, confounding compensation. Furthermore, we run the sample with 7-AAD in the buffer to increase staining intensity (washing it away reduces the intensity about four-fold)
2) Experimental samples—start with $8 \times 10^6$ total cells for untreated and $10^7$ for TNF/IL-1 treated. Stain according to following protocol.
A-549 cells require special handling to resuspend properly. Resuspend pellets by pipeting
up and down with a pipetman until cells appear dispersed. Then vortex.
A. Materials
 01. anti-NF-κB (F6): Santa Cruz Biotechnology (Cat. No. SC-8005), 200 μg/ml
 02. Alexa Fluor488 donkey anti-mouse IgG: Molecular Probes (Cat), 1:1 mg/ml
 03. Streptavidin Alexa Fluor 488: Molecular Probes
 04. Recombinant human TNF-α: BD (Cat#554618. Lot#0000056653)
 05. Recombinant human IL-1β: ebiOscience (Cat#14-8018-62, Lot#)
 06. A549 cells (ATCC No. CCL-I85)
 07. Dulbecco's MEM
 08. Fetal Calf Serum
 09. F-25 Culture Flask
 10. 0.25% trypsin 1 EDTA
 11. Phosphate buffered saline without $Ca^{2+}/Mg^{2+}$ (PBS)
 12. 4% PFA/PBS (Fixation Buffer)
 13. 0.1% triton X-100/PBS (Perm Buffer)
B. Cell Preparation
We used A549 cells cultured in Dulbecco's MEM supplemented with 10% fetal calf serum in an incubator containing 5% $CO_2$ at 37. A-549 cells were stimulated with or without TNF-α and IL-Iβ for 45 min to induce nuclear translocation of NF-κB.
 01. Culture A549 cells in the T-75 $cm^2$ culture flask containing 20 ml of the 10% FCS/
 Dulbecco's MEM.
 02. Stimulate the exponentially growing cells with TNF-α (2.0 ng/ml) and IL-Iβ (10 pg/ml) for 45 min at 37° C. under 5% $CO_2$ humidified atmosphere.
 03. After stimulation, discard media and wash cells with 5-10 ml of PBS.
 04. Add 2 ml of 0.25% trypsin/EDTA to cells, and incubate 37° C. for 1 min or until cells
 have detached.
 05. Suspend cells by adding 8 ml of complete DMEM.
 06. transfer the cell suspension to 15 ml centrifuge tube.
 07. Centrifuge at 300×g 10' 4° C., and remove media.
 08. Fix cells by resuspendjng @ $10^7$ cells/ml in 4% PFA/PBS 30' 4° C.
 09. Wash with PBS, then perm cells by resuspending @ $2 \times 10^7$ cells/ml in 0.1% triton X-
 100/0.02% EDTA/PBS (Perm) 30' 4° C.
 10. Add equal volume of anti-NFOB 20 μg/mL in Perm (final mAb concentration of 10
 μg/mL) 15' 4° C.
 11. Wash Perm Buffer.
 12. Resuspend $10^7$ cells/ml in Perm+AF488 donkey anti-mouse IgG (10 μg/mL) 15' 4° C.
 13. Filter 70 μm mesh and wash with Perm.
 14. Resuspend $5 \times 10^7$ cells/ml Perm+10 μM 7-AAD 5' and run directly on the ImageStream.

Example 2

Induction of Translocation in Non-Adherent Cells

Human monocyte cell line THP-1, obtained from ATCC (Rockville, Md.), were maintained in RPMI 1640 (Gibeo, Grand Island. N.Y.) containing 5% fetal bovine serum, 1 mM sodium pyruvate (Mediatech, Herndon, Va.). 100 μM nonessential amino acids, 100 U/ml penicillin, 100 μg/ml streptomycin. and 2 mM L-glutamine (BioWhittaker. Walkersville, Md.) in 5% $CO_2$ atmosphere at 37° C. The density of exponentially growing cells was less than $3 \times 10^5$ cells per ml at the time of all treatments. To induce NF-κB translocation into the nucleus from the cytoplasm, cells were treated for 1 hr with LPS.

The following is the experimental procedure for LPS-induced Nuclear Translocation of NF-κB in THP-1 cells. Samples:
1) Unstained and single fluorescent color control samples—start with $3.0 \times 10^6$ total cells each. In this experiment. controls are: unstained
NF-κB Alexa Fluor488
7-AAD
At the end, resuspend in 100 μl 0.1% triton X-I00/PBS.
Unstained and NF-κB can be mixed and run as one file, then a separate .rif of unlabeled cells can be created in IDEAS. The 7-AAD control must be run separately, because 7-AAD comes off of labeled cells and stains unlabeled cells, confounding compensation. Furthermore, we run the sample with 7-AAD in the buffer to increase staining intensity (washing it away reduces the intensity about four-fold)
2) Experimental samples—start with $10^7$ total cells for untreated LPS-treated. Stain according to following protocol.
C. Materials
14. anti-NF-κB (F6): Santa Cruz Biotechnology (Cat. No. SC-8008), 200 g/ml
15. Alexa Fluor488 donkey anti-mouse IgG: Molecular Probes (Cat), 1.1 mg/ml
16. Streptavidin Alexa Fluor 488: Molecular Probes
17. Lipopolysaccharide (LPS) from *E. Coli* 0111B4: Sigma (Cat #L2630, Lot#)
18. THP-1 cells
19. RPMI
20. Fetal Calf Serum
21. T-75 $cm^2$ Culture Flask
22. EDTA
23. Phosphate buffered saline without $Ca^{2+}/Mg^{2+}$ (PBS)
24. 4% PFA/PBS (Fixation Buffer)
25. 0.1%-triton X-100/PBS (Perm Buffer)
D. Cell Preparation We used THP-1 cells cultured in RPMI supplemented with 10% fetal calf serum in an incubator containing 5% $CO_2$ at 37. THP-1 cells were stimulated with or without LPS and for 60 min to induce nuclear translocation of NF-κB.
15. Culture THP-1 cells in the T-75 $cm^2$ culture flask containing 50 ml of the 10% FCS/RPMI ($3 \times 10^5$ cells/mL).
16. Stimulate the exponentially growing cells with LPS for 60 min at 37° C. under 5% $CO_2$ humidified atmosphere.
17. Centrifuge at 300×g 10' 4° C., and remove media.
18. Fix cells by resuspending @ $10^7$ cells/ml in 4% PFA/PBS 30' 4° C.
19. Wash with PBS, then perm cells by resuspending @ $2 \times 10^7$ cells/ml in 0.1% triton X-100/0.02% EDTA/PBS (Perm) 30' 4° C.
20. Add equal volume of anti-NF-κB 20 μg/mL in Perm (final mAb concentration of 10 μg/mL) 15' 4° C.
21. Wash Perm Buffer.
22. Resuspend $10^7$ cells/ml in Perm+AF488 donkey anti-mouse IgG (10 μg/mL) 15' 4° C.
23. Filter 70 μm mesh and wash with Perm.
24. Resuspend $5 \times 10^7$ cells/ml Perm+10 μM 7-AAD 5' and run directly on ImageStream.

Example 3

Nuclear Staining and NF-κB Staining

Control (untreated) cell and LPS or IL-1β/TNF-α. treated cells were independently counted and washed once in phosphate buffered saline (PBS, Fair Lawn, N.J.). Each cell group was resuspended at $10^7$ cells/ml in 10 μM 7-aminoactinomycin D (7-AAD, Molecular Probes) for 10 minutes at room temperature. Cells were additionally stained with anti-NF-κB mAb—AF488 donkey anti-mouse IgG. Each cell group was washed, fixed in 2% paraformaldehyde (Sigma), and. analyzed by flow cytometry and immunofluorescence microscopy.

Example 4

Conventional Flow Cytometry and Imaging Flow Cytometry

For flow cytometry, cell fluorescence data excited by a 488 nm laser were acquired using the FACSort™ cytometer (BD Immunocytometry Systems. San Jose. Calif.) and analyzed using CellQuest™ (BD Immunocytometry Systems). For imaging flow cytometry, fixed cells at $5 \times 10^7$ cells per ml were run at 100 cells per second on an ImageStream100™ ("Beta" version), and the data analyzed using the ImageStream Data Analysis and Exploration Software™ (IDEAS™)

Example 5

Instrumentation for Multispectral Imaging Flow Cytometry

FIG. 1 provides an exemplary layout of the ImageStream™ platform. Cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see. e.g., U.S. Pat. No. 6,249,341). With this technique, the multispectral image is optically decomposed into a set of 6 sub-images, each corresponding to a different color component and spatially isolated from the remaining sub-images. This is exemplified in FIG. 1, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD is operated using time-delay-integration (TDI), in which image photons converted to photocharges in an array of pixels are continuously shifted (at a rate synchronized with the velocity of the flowing cell's image) from pixel to pixel down the detector and parallel to the axis of flow to avoid image streaking. For example, the instrument can operate at a continuous data rate of approximately 30 megapixels per second and integrate signal from each object for 10 milliseconds, which allows the detection of even faint fluorescent probes within cell images that are acquired at high speed. Attention to pump and fluidic system design to achieve highly laminar, non-pulsatile flow can eliminate cell rotation or lateral translation on the time scale of the imaging process (see, e.g., U.S. Pat. No. 6,532,061). Every pixel read from the CCD is analyzed by a real-time algorithm that detects the presence of object images and calculates a number of basic morphometric and photometric features, which can be used as criteria for data storage. Data files encompassing 10,000-20,000 cells can be about 100 MB in size, and are stored and analyzed using standard personal computers.

Example 6

Immunofluorescence Microscopy

Fixed control and treated cells were placed on a conventional glass slide (Erie Scientific, Portsmouth, N.H.), mixed 1:1 with Antifade (Molecular Probes) and covered with a cover slip. The cells were visualized at 400× using an Eclipse E600 (Nikon, Melville, N.Y.) fluorescence microscope equipped with filters appropriate for Alexa Fluor 488 (535/40 nm emission) and 7-AAD (630/60 nm emission).

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for measuring molecular movement in a cell, comprising:
    contacting the cell with at least one marker;
    imaging the cell with a detector;
    creating a mask; and
    measuring the molecular movement in the cell based at least in part on a correlation between the mask and the at least one marker.
2. The method of claim 1 wherein there is relative motion between the cell and the detector.
3. The method of claim 1 wherein the at least one marker is a fluorescent labeled antibody.
4. The method of claim 1 wherein the at least one marker is a fluorescent molecule.
5. The method of claim 1 wherein the mask is a compartment mask and the compartment is nucleus, cytoplasm, or membrane.
6. The method of claim 1 wherein the at least one marker is marked NF-κB.
7. The method of claim 1 further comprising the step of inducing molecular movement in the cell.
8. The method of claim 7 wherein the induced molecular movement is nuclear translocation.
9. The method of claim 7 wherein the molecular movement is induced with LPS or IL-1β/TNF-α.
10. A method for measuring nuclear translocation in a cell, comprising:
    contacting the cell with at least one marker;
    imaging the cell with a detector;
    creating a nuclear mask; and
    measuring the nuclear translocation in the cell based at least in part on a correlation between the nuclear mask and the at least one marker.
11. The method of claim 10 wherein there is relative motion between the cell and the detector.
12. The method of claim 10 further comprising the step of inducing molecular movement in the cell.
13. The method of claim 12 wherein the induced molecular movement is the nuclear translocation.
14. The method of claim 12 wherein the molecular movement is induced with LPS or IL-1β/TNF-α.
15. The method of claim 10 wherein the at least one marker is 7-AAD.
16. The method of claim 10 wherein the at least one marker is marked NF-κB.
17. The method according to any one of claims 1-16 wherein the detector is a time delay integration charge-coupled detector.
18. A system configured to perform the method according to claim 1 or claim 10.
19. An imaging system adapted to measure molecular movement in a cell, comprising:
    a light source that produces light incident on the cell, the cell contacted with at least one marker;
    a collection lens disposed so that light emitted by the light source and traveling from the cell passes through the collection lens and travels along a collection path;
    a spectral decomposition optical system disposed so that light traveling along the collection path is separated into multiple spectral bands;
    a detector disposed to receive the multiple spectral bands, producing a first signal corresponding to a first one of the multiple spectral bands and producing a second signal corresponding to a second one of the multiple spectral bands; and
    a processor configured to measure the molecular movement in the cell based at least in part on a correlation between the first signal and the second signal.
20. The imaging system of claim 19, wherein the light source is a spectrally-limited light source.
21. The imaging system of claim 19, wherein the light that has passed through the collection lens is dispersed in a plane that is orthogonal to a direction of relative movement between the cell and the imaging system.
22. The imaging system of claim 19, wherein the detector is a time delay integration charge-coupled detector.
23. The imaging system of claim 19, wherein the detector produces the first signal and the second signal simultaneously.
24. The imaging system of claim 19, wherein the first one of the multiple spectral bands corresponds to a spectral band of the cell contacted with the at least one marker.
25. The imaging system of claim 19, wherein the second one of the multiple spectral bands corresponds to a spectral band for a specific cellular compartment of the cell.

26. The imaging system of claim 19, wherein the processor is further configured to create an image mask from the second signal.

\* \* \* \* \*